United States Patent
Endo et al.

(10) Patent No.: US 6,316,242 B1
(45) Date of Patent: Nov. 13, 2001

(54) METHOD FOR PRODUCING NITRILE HYDRATASE

(75) Inventors: Isao Endo, Kokubuniji; Masafumi Yohda; Masafumi Odaka, both of Wako; Masaki Nojiri, Tsurugashima, all of (JP)

(73) Assignee: The Institute of Physical and Chemical Research (JP)

( * ) Notice: Subject to any disclaimer, the term of this patent is extended or adjusted under 35 U.S.C. 154(b) by 0 days.

(21) Appl. No.: 09/369,170

(22) Filed: Aug. 5, 1999

(30) Foreign Application Priority Data

Aug. 6, 1998 (JP) .................................................. 10-222837

(51) Int. Cl.⁷ ...................................................... C12N 9/88
(52) U.S. Cl. ...................... 435/232; 435/691; 435/235.1; 435/252.33; 536/23.2; 536/23.7
(58) Field of Search .................................. 435/71.1, 69.1, 435/232, 252.33, 235.1; 536/23.2, 23.7

(56) References Cited

U.S. PATENT DOCUMENTS 5,731,176 * 3/1998 Yamada et al. ...................... 435/129

OTHER PUBLICATIONS

Kobayashi, M., T. Nagasawa, and H. Yamada. Enzymatic synthesis of acylamide: a success story not yet over. Trends Biotechnol. 1992 Nov.; 10(11): 402–8.*

Yamada, H., and M. Kobayashi. Nitril Hydratase and its application to industrial production of acrylamide. Biosci. Biotech. Biochem., 60(9), 1391–1400, Sep. 1996.*

Nojiri, M., M. Yohda, M. Odaka, Y. Matsushita, M. Tsujimura, T. Yoshida, N. dohmae, K. Takio, and I. Endo. Funciontal Expression of Nitrile Hydratase in *Escherichia coli*: Requirement of a Nitrile Hydratase Activator . . . J. Bichem. 124, 696–704, Apr., 1999.*

Hashimoto et al., "Cloning and Characterization of an Amidase Gene from Rhodococcus Species N–774 and Its Expression in *Escherichia coli*", *Biochem. Biophy. Acta* vol. 1088, No. 2, pp. 225–233 (Feb. 16, 1991).

Hashimoto et al., "Nitrile Hydratase Gene from Rhodococcus sp. N–774 Requirment for its Downstream Region for Efficient Expression", *Biosci. Biotechnol. Biochem* vol. 58, No. 10, pp. 1859–1865 (Oct. 1994).

* cited by examiner

Primary Examiner—Nashaat T. Nashed
Assistant Examiner—Christian L. Fronda
(74) Attorney, Agent, or Firm—Burns, Doane, Swecker & Mathis, L.L.P.

(57) ABSTRACT

There is disclosed a method for producing nitrile hydratase comprising culturing a transformant cell which is obtained by transforming a host cell of bacterium not belonging to the genus Rhodococcus with a vector (1) which contains a nucleotide sequence encoding at least the α a chain and the β chain of nitrile hydratase, or the vector (1) and a vector (2) which contains a nucleotide sequence encoding at least the β chain of the nitrile hydratase, and collecting produced nitrile hydratase, wherein the culture of the transformant cell is performed at a temperature of 35° C. or less.

5 Claims, 1 Drawing Sheet

METHOD FOR PRODUCING NITRILE HYDRATASE

BACKGROUND OF THE INVENTION

1. Field of the Invention

Figure 1:
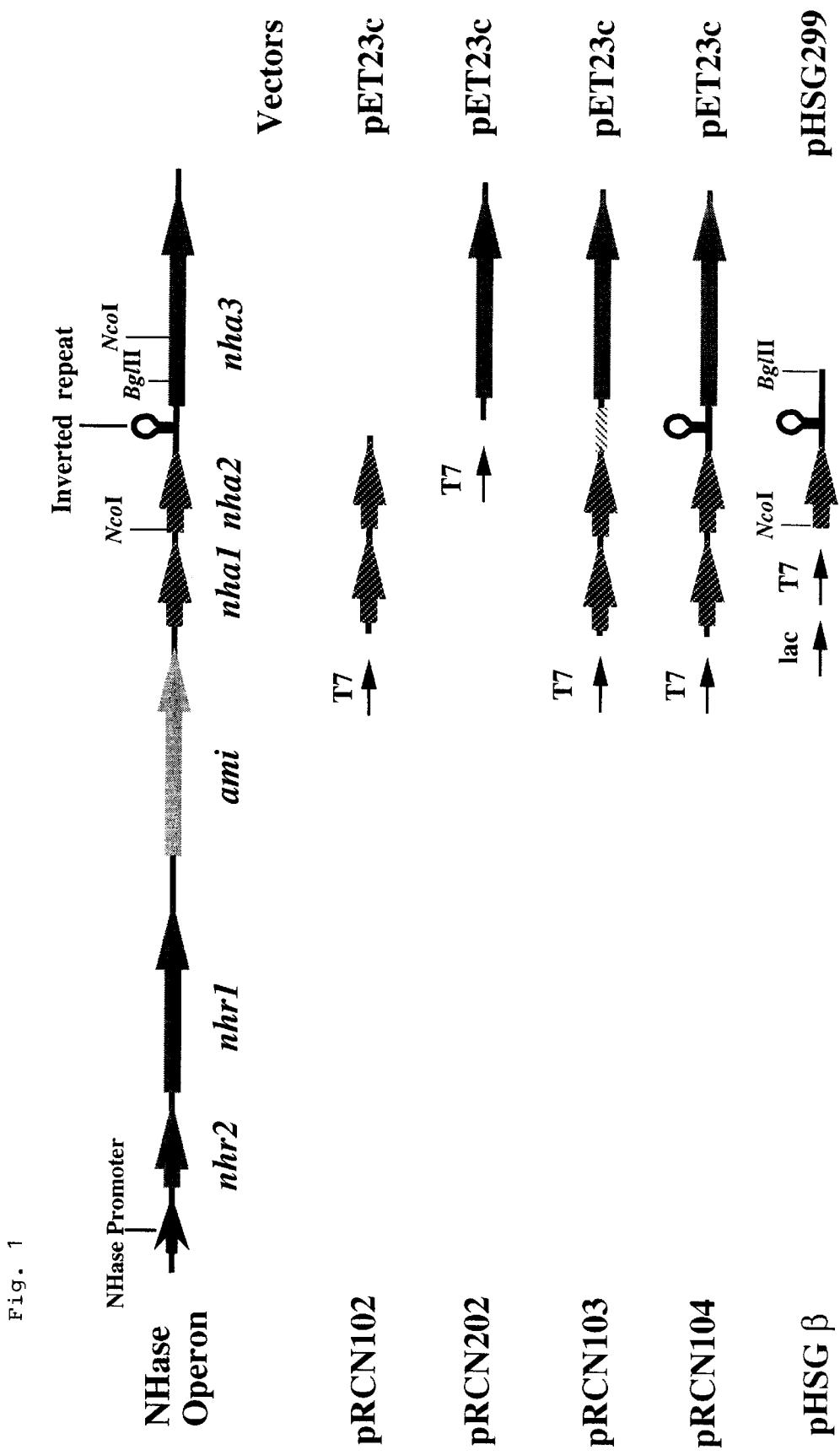

The present invention relates to a method for producing nitrile hydratase (NHase) utilizing a host of bacterium not belonging to the genus Rhodococcus.

2. Description of Related Art

Nitrile hydratase (NHase) is an enzyme that is produced in microorganisms and converts a nitrile compound into an amide compound by hydration. It is a soluble metalloprotein containing iron or cobalt atom in its active center. NHases have been isolated from several kinds of bacterial cells, and all of them consist of two kinds of subunits, α and β. Both of the subunits have a molecular weight of about 23,000. It has also been reported that NHase derived from Rhodococcus sp. N-771 strain has a non-heme iron center of mononuclear low-spin six coordinate Fe(III). NHases of Rhodococcus sp. N-771, N-774 and R312 are considered to be the same enzyme because their nucleotide sequences are identical to one another, and their enzymatic activity varies with light irradiation. That is, when bacterial cells exhibiting high activity are left in the dark, the enzyme activity is reduced, and the activity is increased again by photo-irradiation. This is because, in the dark, nitric oxide produced from the cell bonds to the active center of the iron type nitrile hydratase, i.e., the non-heme iron center, to produce an inactive state. When the iron type nitrile hydratase in this inactive state is irradiated by light, NO is instantly dissociated, and the iron type nitrile hydratase is activated. The above binding characteristic of NO is commonly observed for substantially all of the iron type nitrile hydratases.

The present inventors are attempting to apply the above photoreactive iron type nitrile hydratase derived from Rhodococcus bacteria to, for example, increasing efficiency of amide production, photoreactive amide production and the like. To this end, however, it is necessary to improve the iron type nitrile hydratase derived form Rhodococcus bacteria, for example, to further enhance its catalytic ability. To improve the catalytic ability, it can be expected to use genetic recombination techniques utilizing a widely usable host such as *Escherichia coli*. In fact, the nitrile hydratase gene has been isolated, and the production of the enzyme by utilizing *Escherichia coli* has also been reported. However, according to the previous reports, when *Escherichia coli* was used as a host, the specific activity per unit weight was lower than that obtained by utilizing a Rhodococcus bacterium as the host. Therefore, Rhodococcus host vector systems have conventionally been used in general. However, handling of Rhodococcus bacteria is more difficult compared with *Escherichia coli* and the like. In addition, since any potential promoter therefor is not available, they suffer from problems, for example, sufficient increase of activity can not be obtained.

As mentioned above, various reports have previously been made for the recombinant production of nitrile hydratase utilzing *Escherichia coli*. According to those reports, it has been elucidated that, in both of the iron type and cobalt type nitrile hydratases, it is required for their expression to co-express another gene which is present in the nitrile hydratase operon in addition to the genes for the α and β subunits constituting nitrile hydratase. As for the cobalt type nitrile hydratase, the nitrile hydratase has been successfully produced by simultaneously introducing these three kinds of genes into *Escherichia coli*. A similar approach was expected to be effective as also for the iron type enzyme, and the nitrile hydratase from a Pseudomonas bacterium has successfully produced in *Escherichia coli*.

However, the aforementioned methods cannot be considered to be an efficient method. In addition, when the photoreactive iron type nitrile hydratase derived form Rhodococcus bacteria is produced by using *Escherichia coli* as the host, most of the produced nitrile hydratase precipitates, and therefore the activity of the recombinant cell becomes extremely low. Therefore, it is difficult to practically utilize the produced nitrile hydratase in such a method, which has been a serious obstacle for utilization of the photoreactivity.

However, if it becomes possible to efficiently produce the photoreactive iron type nitrile hydratase derived from Rhodococcus by using *Escherichia coli*, it will enable to enhance the catalytic ability, and make it easy to utilize the enzyme for increasing amide production efficiency and the photoreactive amide production.

SUMMARY OF THE INVENTION

Therefore, the object of the present invention is to provide a method for producing nitrile hydratase using a host of bacterium not belonging to the genus Rhodococcus.

The present invention relates to a method for producing nitrile hydratase comprising culturing a transformant cell which is obtained by transforming a host cell of bacterium not belonging to the genus Rhodococcus with a vector (1) which contains a nucleotide sequence encoding at least the α chain and the β chain of nitrile hydratase, or the vector (1) and a vector (2) which contains a nucleotide sequence encoding at least the β chain of the nitrile hydratase, and collecting produced nitrile hydratase, wherein the culture of the transformant cell is performed at a temperature of 35° C. or less.

FIG. 1 shows characteristics of each plasmid used in Example 1.

PREFERRED EMBODIMENTS OF THE INVENTION

In the method for producing nitrile hydratase of the present invention, first constructed are the vector (1) which contains a nucleotide sequence encoding at least the α chain and the β chain of nitrile hydratase, and, if required, the vector (2) which contains a nucleotide sequence encoding at least the β chain of nitrile hydratase. Subsequently, a host cell is transformed with these vectors. The host cell is a cell of bacterium other than those belonging to the genus Rhodococcus. Furthermore, the obtained transformant is cultured at a temperature of 35° C. or less, and nitrile hydratase is collected.

Known sequences can be used for the nucleotide sequences encoding the α chain and the β chain of nitrile hydratase which are used for the construction of the vector (1). For example, gene sequences for the α chain and the β chain of the nitrile hydratase derived from Rhodococcus N-771 strain are described in Biochem. Biophys. Acta Feb. 16, 1991; 1088(2):225–233, Cloning and characterization of an amidase gene from Rhodococcus species N-774 and its expression in *Escherichia coli.*, Hashimoto Y, Nishiyama M, Ikehata O, Horinouchi S, and Beppu T. Further, orf1188 sequence which is another gene present in the operon and required for the expression of nitrile hydratase can be simultaneously used in the aforementioned vector (1). Orf1188 is a gene encoding an activator of nitrile hydratase, which participates in the formation of the active center, i.e., the non-heme iron center. As the function of the activator of nitrile hydratase, two kinds of functions, transportation of iron and oxidation of cysteine of the active center, are expected. A sequence containing the gene for this activator has also been known. For example, a sequence described in Biosci. Biotechnol. Biochem. October 1994; 58 (10):1859–1865, Nitrile hydratase gene from Rhodococcus sp. N-774 requirement for its downstream region for efficient expression., Hashimoto Y, Nishiyama M, Horinouchi S, and Beppu T. can be used.

As the nucleotide sequence which encodes the β chain of the nitrile hydratase used for the construction of the vector (2), a sequence similar to the sequence of the gene which encodes the aforementioned β chain used for the vector (1) can be used. As the vector used for the construction of the vector (2), a vector having antibiotic resistance different from that of the vector used for the vector (1) should be used. This is because, when two or more kinds of plasmids are used together and simultaneously expressed, it is necessary to use vectors each containing a gene for different antibiotic resistance.

A host cell of bacterium other than those belonging to the genus Rhodococcus, for example, *Escherichia coli*, is transformed with the constructed vector (1), or the vectors (1) and (2). The transformation can be carried out in a conventional manner. However, when the vectors (1) and (2) are expressed simultaneously, two kinds of antibiotics, for which the vectors have resistance, are added to a culture medium. The co-expression of the vectors (1) and (2) increases the β chain production amount, and consequently increases activated nitrile hydratase.

The culture of the transformant can be performed under the same conditions as usual culture of *Escherichia coli* except that it is carried out at a temperature of 35° C. or less. The culture temperature is preferably in a range of 25–35° C., more preferably 25–32° C. Although the reason is not clarified, at 37° C., which is widely used as the culture temperature of *Escherichia coli*, most of the nitrile hydratase is expressed as an insoluble enzyme, and thus it substantially does not show the activity, whereas at 35° C. or less, in particular 32° C. or less, the activity of the nitrile hydratase is markedly enhanced. Although the culture is possible at 25° C. or less, it is not so desirable because growth rate is markedly decreased.

Hereafter, the present invention will be explained in more detail.

(1) Method for Construction of Vector (1) Containing Genes for α Chain and β Chain of Nitrile Hydratase and Gene for Activator The sequences of the genes for the α and β chains of the nitrile hydratase of the Rhodococcus N-771 strain and the gene for the activator have been known. Therefore, by synthesizing primers based on such sequences and performing PCR using the total DNA as template, vectors having the genes for the α and β chains of nitrile hydratase and the gene for the activator can readily be obtained. These genes constitute one operon containing the genes for the α chain, the β chain, and the activator in this order. By introducing a DNA fragment containing from the initiation codon for the α chain gene to the genes for the β chain and the activator into an *Escherichia coli* expression vector such as pET23c at the downstream from its promoter, an expression plasmid for *Escherichia coli* can be constructed.

In order to produce an iron type nitrile hydratase of a strain of which genetic nucleotide sequence is unknown, i.e., a strain other than Rhodococcus N-771 strain, it is necessary to isolate its gene and determining its sequence. Because the sequences of iron type nitrile hydratases resemble one another, DNA primers are synthesized based on highly homologous regions, and a gene fragment is amplified by PCR utilizing the total DNA as template. The nitrile hydratase gene operon is isolated from a gene library by colony hybridization using the above gene fragment as a probe. The gene library is produced by digesting the total DNA with restriction enzymes such as EcoRI and HindIII, and introducing the obtained fragments into vectors such as pUC18. The obtained gene fragments are digested with a suitable restriction enzyme into smaller fragments, and the whole nucleotide sequence is determined. The sequences encoding the α and β chains and the activator can be determined through computerized analysis of the sequence. The construction of expression system thereafter can be performed in the same manner as that for N-771.

(2) Method for Constructing Vector (2) Containing Gene Encoding β Chain of Nitrile Hydratase Because the sequence of the gene for the β chain of nitrile hydratase of the Rhodococcus N-771 strain is known, a vector containing the gene for the β chain of the nitrile hydratase can easily be obtained in a manner similar to that described in the above (1), i.e., by synthesizing primers based on the sequence, and performing PCR utilizing the total DNA as template. The gene contains the genes for the α chain, the β chain and the activator in this order, and constitute one operon. As for the construction of a vector for the β chain, an expression plasmid for *Escherichia coli* can be constructed by introducing a DNA fragment containing the gene for the β chain into an *Escherichia coli* expression vector such as pHSG299 at the downstream from its promoter.

When co-expression of the vector (1) and the vector (2) is intended, a vector having antibiotic resistance different from that of the vector (1) is used for the vector (2). As the antibiotic for the marker, for example, ampicillin, kanamycin, chloramphenicol, tetracycline and the like can be mentioned.

In order to separately produce each of the subunits and the activator of an iron type nitrile hydratase of a strain of which genetic nucleotide sequence is unknown, i.e., a strain other than Rhodococcus N-771 strain, it is necessary to isolate each gene and determining its sequence like in the above (1). Identification of the genes encoding each subunit and the activator of the iron type nitrile hydratase of the unknown strain can be performed in a manner similar to that of the above (1). The construction of expression system thereafter can be performed in the same manner as that for N-771.

(3) Method for Culturing Transformant

When a nitrile hydratase expression system to be used utilizes T7 promoter like pET vector, the vector is transformed into an *Escherichia coli* which produces T7 polymerase upon IPTG induction, for example, JM109 (DE3) strain.

In order to attain expression of nitrile hydratase, the transformant is inoculated to a culture medium such as LB medium containing an antibiotic, and the expression is induced by adding IPTG during the logarithmic phase. When two or more kinds of vectors are expressed simultaneously, antibiotics for each vector are added to the culture medium. The duration from the induction of the expression to harvest of the cells should be changed depending on the nature of the protein. While a longer culture time affords a larger amount of synthesized protein, a ratio of the protein degraded by protease increases on the other hand. Therefore, optimum culture time can be decided by measuring actual expression amount.

(4) Method for Collecting Nitrile Hydratase from Culture

The cultured *Escherichia coli* is harvested by centrifugation. The harvested *Escherichia coli* is suspended in a buffer (e.g., 50 mM HEPES buffer, pH 7.5) and the like, disrupted by sonication, and centrifuged. Because nitrile hydratase is a soluble enzyme, active nitrile hydratase is contained in the supernatant. This extract is subjected to liquid chromatography, which may use various columns, to perform separation and purification of the nitrile hydratase. As the column, an ion exchange column such as DEAE-Toyopearl, hydrophobic interaction column such as Butyl-Toyopearl, gel filtration column such as Toyopearl and the like may be used.

EXAMPLES

Example 1

A nitrile hydratase operon gene was isolated from Rhodococcus sp. N-771 by colony hybridization. Genes encoding the α chain and the β chain and a gene encoding the activator, usually called orf1188, which is present in the downstream of the gene encoding the β chain, were amplified by PCR, and introduced into *Escherichia coli* vectors pET23c and pHSG299 to produce four kinds of expression vectors pRCN102, pRCN103, pRCN104, and pHSGβ. The characteristics of each plasmid are shown in FIG. 1. The pRCN102 consisted of pET23c containing the introduced genes for the α chain and the β chain in the downstream of the T7 promoter of pET23c, and the pRCN103 and pRCN104 consisted of pET23c containing the introduced genes for the α chain, the β chain and the activator in the downstream of the T7 promoter of pET23c. In the pRCN103, a sequence forming hairpin structure present between the β chain gene and the activator gene was eliminated in order to increase expression efficiency of the activator gene. The PHSGβ consisted of pHSG299, which is a kanamycin resistant vector, introduced with the gene for the β chain in the downstream of the lac promoter of pHSG299.

*Escherichia coli* JM109 (DE3) was transformed with each plasmid, and cultured. As the culture medium, Luria Broth (LB) culture medium was used. When transformation was carried out with pRCN102, pRCN103, or pRCN104 alone, ampicillin was added to the culture medium at 150 μg/ml. When transformation was performed simultaneously with pHSGβ, ampicillin and kanamycin were added to the culture medium at 150 μg/ml for each. The culture was carried out at 37° C., 30° C., and 27° C., and IPTG (isopropyl-β-thiogalactopyranoside) and iron citrate were added to the medium at 0.1 mM and 2 mM, respectively, when the cell concentration reached 0.5 in terms of absorbance at 600 nm. After the culture was further continued for 12 hours at the same temperature, the *Escherichia coli* cells were harvested by centrifugation (5000×g, 10 min, 4° C.), and suspended in 50 mM HEPES puffer, pH 7.5. The suspension was subjected to cell disruption by sonication and separation by centrifugation to obtain a crude extract. The nitrile hydratase activity of this crude extract was measured by using methacrylonitrile as a substrate (Table 1). In this case, activity converting 1 μmol of methacrylonitrile into methacrylamide per 1 minute was defined as 1 unit.

TABLE 1

Nitrile hydratase activity in extract containing plasmid but not containing cells of *E. coli* transformant

| Plasmid | Nitrile hydratase activity (unit/mg) | | |
|---|---|---|---|
| | 37° C. | 30° C. | 27° C. |
| pRCN102 | ND[a] | ND | — |
| pRCN103 | ND | 11.0 | — |
| pRCN104 | ND | 109.0 | — |
| pRCN102 + pHSGβ | ND | ND | ND |
| pRCN103 + pHSGβ | ND | 184.6 | 411.8 |
| pRCN104 + pHSGβ | ND | 117.2 | 452.2 |

[a]ND: Not detectable

The nitrile hydratase activity of purified native nitrile hydratase and transformation type nitrile hydratase was 1732.9 units/mg and 1635.0 units/mg, respectively.

When the cells were cultured at the temperature of 37° C., which is generally used for the culture of *Escherichia coli*, no nitrile hydratase activity was observed in any of the recombinant cells. When analyzed by SDS-PAGE, the α and β subunits were found to be expressed as denatured insoluble proteins in all of the transformant cells. However, when the culture temperature was lowered to 30° C. and the activator was co-expressed, marked nitrile hydratase activity was confirmed. Further, as for pRCN103, marked increase of the activity was observed when pHSG β was co-expressed. This increase was confirmed to be arisen from considerable difference of the produced amounts of the α and β chains when pRCN103 was used alone, based on the results of SDS-PAGE. When the culture was performed at 30° C., a major part of nitrile hydratases in *Escherichia coli* was still in the insoluble fraction, and thus it was suggested that there was room for further improvement.

Therefore, the culture temperature was further lowered to 27° C., and specific activity of 400 U/mg or more could be obtained for both cases of pRCN103+pHSGβ and pRCN104+pHSGβ. Because the specific activity of the purified enzyme was about 1700 U/mg, about 25% of the soluble protein was the nitrile hydratase. This production amount can be considered sufficient based on comparison with that obtained in production of other enzymes by *Escherichia coli*, or the production of the nitrile hydratase using Rhodococcus or the like. Also in this case, the nitrile hydratase still remained in the insoluble fraction, and it was considered to be caused by excessive production of the enzyme due to the potential promoter.

What is claimed is:

1. A method for producing nitrile hydratase comprising culturing a transformant cell which is obtained by
    transforming an *E. coli* cell with a vector (1) which contains a nucleotide sequence encoding at least the α subunit and β subunit of nitrile hydratase of Rhodococcus N-771, and a nucleotide sequence encoding an activator for the nitrile hydratase; and
    collecting produced nitrile hydratase,
wherein the culture of the transformant cell is performed at a temperature of about 27° C.

2. A method for producing nitrile hydratase comprising culturing a transformant cell which is obtained by
    transforming an *E. coli* cell with a vector (1) which contains a nucleotide sequence encoding at least the α subunit and β subunit of nitrile hydratase of Rhodococcus N-771, and a nucleotide sequence encoding an activator for the nitrile hydratase and a vector (2) which contains a nucleotide sequence encoding at least the β subunit of the nitrile hydratase but not the α subunit; and collecting produced nitrile hydratase,
wherein the culture of the transformant cell is performed at a temperature of about 35° C. or less.

3. The method of claim 2 wherein the culture of the transformant cell is performed at a temperature within a range of 25 to 35° C.

4. The method of claim 2, wherein the culture of the transformant cell is performed at a temperature of 32° C or less.

5. The method of claim 2, wherein the culture of the transformant cell is performed at a temperature of 30° C. or less.

* * * * *